(12) United States Patent
Zook et al.

(10) Patent No.: US 6,432,721 B1
(45) Date of Patent: Aug. 13, 2002

(54) MESO SNIFFER: A DEVICE AND METHOD FOR ACTIVE GAS SAMPLING USING ALTERNATING FLOW

(75) Inventors: J. David Zook, Golden Valley; Cleopatra Cabuz, Edina, both of MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 09/430,425

(22) Filed: Oct. 29, 1999

(51) Int. Cl.[7] .............. G01N 1/22; G01N 1/24; G01N 1/26
(52) U.S. Cl. .......... 436/181; 436/180; 422/82; 422/83; 73/863
(58) Field of Search ............... 436/181, 180; 422/81, 82, 83; 73/863

(56) References Cited

U.S. PATENT DOCUMENTS

| | | | |
|---|---|---|---|
| 4,997,627 A | * 3/1991 | Bergkuist et al. | 422/81 |
| 5,133,937 A | * 7/1992 | Frackelton et al. | 422/81 |
| 5,158,868 A | * 10/1992 | Bergkuist et al. | 435/4 |
| 5,180,288 A | 1/1993 | Richter et al. | |
| 5,659,171 A | * 8/1997 | Young et al. | 250/289 |
| 5,720,330 A | * 2/1998 | Schmalz, Jr. | 141/26 |
| 5,758,823 A | * 6/1998 | Glezer et al. | 239/4 |
| 5,836,750 A | 11/1998 | Cabuz | 417/322 |
| 5,875,823 A | * 3/1999 | Porter | 141/26 |
| 5,900,216 A | * 5/1999 | Nickens et al. | 422/168 |
| 6,037,592 A | * 3/2000 | Sunshine et al. | 250/343 |
| 6,082,185 A | * 7/2000 | Saaski | 73/64.56 |
| 6,096,274 A | * 8/2000 | Hoogendijik et al. | 422/75 |

FOREIGN PATENT DOCUMENTS

| | | |
|---|---|---|
| CH | 579418 A | 9/1976 |
| EP | 0372429 A | 6/1990 |
| EP | 0816677 A | 1/1998 |
| WO | 9419609 A | 9/1994 |
| WO | 9729283 A | 8/1997 |

OTHER PUBLICATIONS

Tupperware advertisement for a Turkey Baster.*
Smith BL, Glazer A, "Formation and Evolution of Synthetic Jets" Phy.Fluids, vol. 10, pp 2281–2297, 1988.
Meso Sniffer White Pages DARPA, Submitted Jan. 18, 1999 Presented Feb. 16, 1999 Cleopatru Cabuz.

* cited by examiner

Primary Examiner—Jill Warden
Assistant Examiner—Jennine Brown
(74) Attorney, Agent, or Firm—Kris T. Fredrick

(57) ABSTRACT

A sampling system for detecting an analyte, comprising a diaphragm pump, a buffer chamber, a sensor head and intake port. The pump includes a chamber for receiving fluids via first and second ports. A buffer chamber is located at the second port for holding a quantity of air, and a sensor head is adapted to identify the presence of a desired analyte and produce a signal in response to the quantity identified. Preferably the diaphragm pump has a volume of gas per stroke capacity slightly larger than the volume of the sensor head such that the pump chamber has a greater volume than the buffer chamber and the buffer chamber has about the same volume as the sensor head. A sensor intake port intakes a sample potentially containing the analyte for contact with the sensor head upon operation of the diaphragm pump and out of the sensor head by jet-action caused by rapid movement of the diaphragm pump. A filter may be used for filtering air drawn through the pump chamber. The diaphragm pump may be either a single chamber pump or a multiple chamber diaphragm mesopump. In the purging mode, the system can also contain a pump for filling the system with cleaned air. When a mesopump is used, a single pumping channel can provide both AC and DC operation.

19 Claims, 4 Drawing Sheets

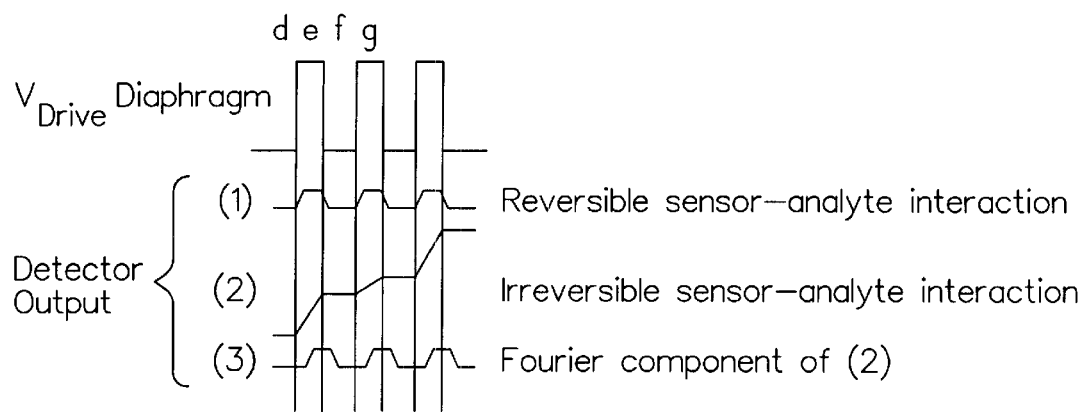
Fig-2
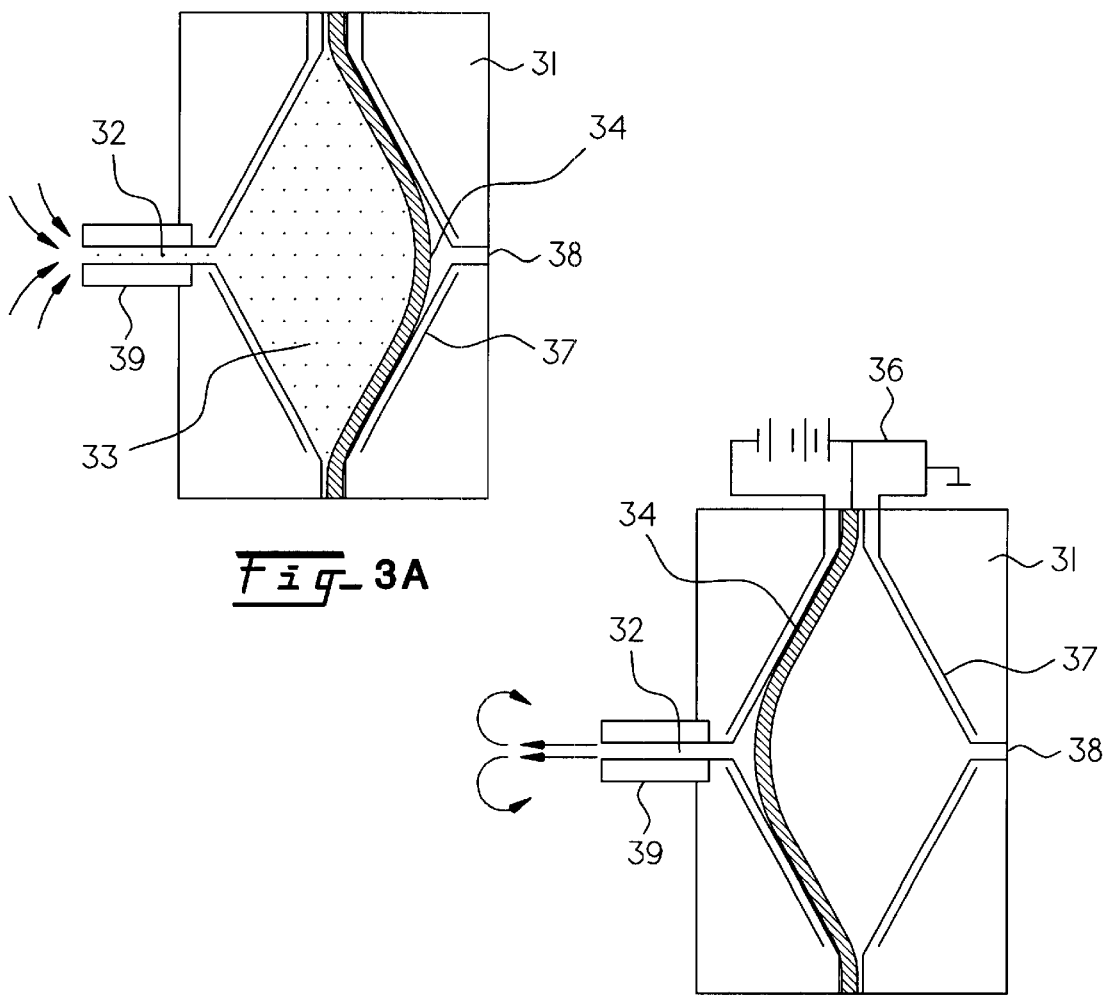
Fig-3A
Fig-3B

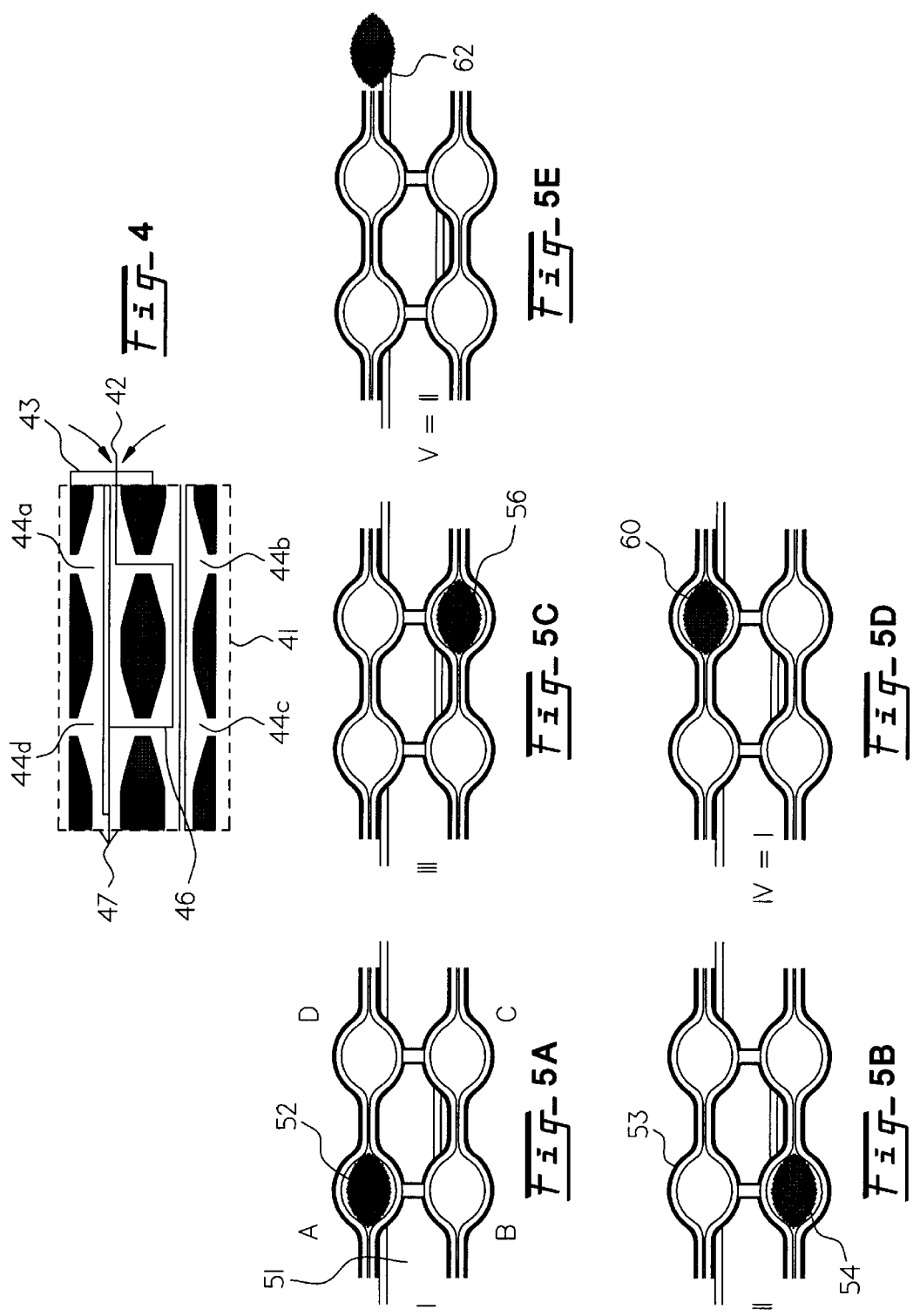

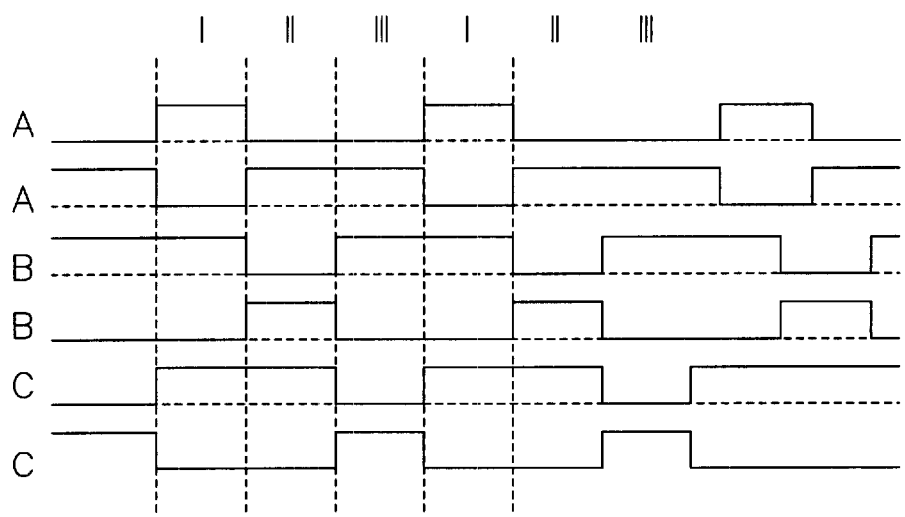
_Fig_6
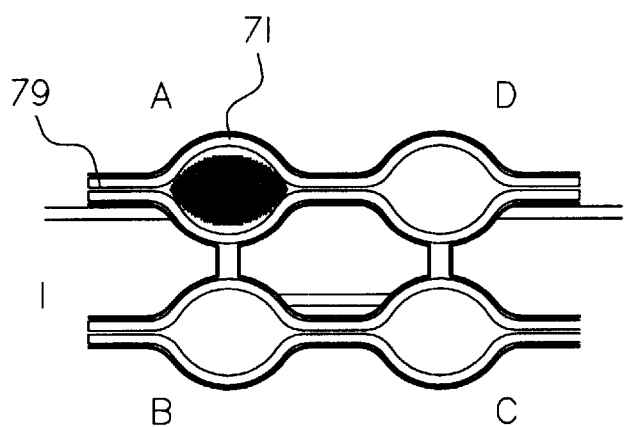
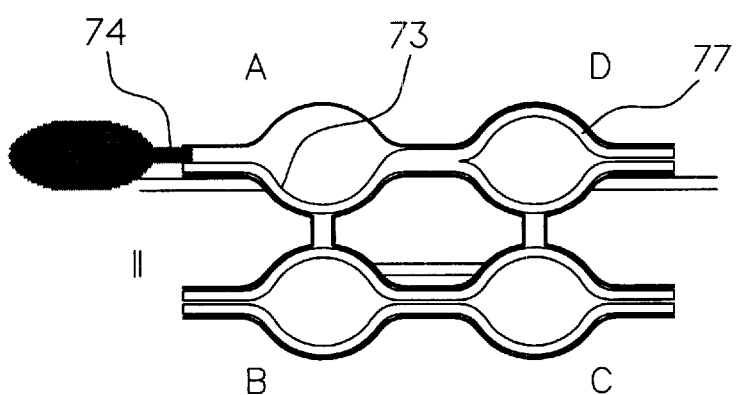
_Fig_7

MESO SNIFFER: A DEVICE AND METHOD FOR ACTIVE GAS SAMPLING USING ALTERNATING FLOW

FIELD OF THE INVENTION

The present invention relates to a sampling pump for a chemical sensing system. More particularly the invention relates to a sensing system using a sniffing mode, alternately inhaling and exhaling in each pumping cycle to expose the sensor or other chemically responsive surface to doses of reference gas and analyte.

BACKGROUND OF THE INVENTION

A large number of chemical and biological sensors are based on changes in the properties of a chemically sensitive material, such as changes in conductivity, surface charge or luminescence, that occur upon adsorption of analyte molecules. Analytes are, of course, the gas to be chemically analyzed. These changes can be monitored through physical methods and are related to the concentration of the analyte in the environment. In order to reduce the time associated with the diffusion of the analyte to the sensor site and to increase the amount of analyte seen by the sensor, sampling methods are used which force the air from the environment into direct contact with the sensitive polymer or other sensor material.

A typical present day configuration includes a material having physical properties that change when its surface is exposed to a gas containing certain chemical or biological species. These properties may be optical, electrical or mechanical, for example. A gas sampling system is used to bring fresh gas samples into contact with the surface of the material. Then, a read-out and signal processing system of electronics is used to convert the physical change to a useful output.

While these sensors have been demonstrated to work over a short time basis, they have been found to be adversely affected by long term drift that limits their practical use. The baseline drift frequently exceeds the minimum detectable signal by orders of magnitude, so that a sensitive technique is rendered essentially useless. It would be of great advantage to the art to greatly reduce the effects of baseline drift in gas sensing systems.

It would be another great advance in the art if a system would be developed to enable or significantly enhance the use of a wide variety of chemical and biological sensing techniques now not useful due to an inability to distinguish between the response to an analyte and the effect of baseline drift.

Other advantages will appear hereinafter.

SUMMARY OF THE INVENTION

It has now been discovered that the above and other objects of the present invention may be accomplished in the following manner. Specifically, the present invention provides a sampling system for a chemical sensor that works in a sniffing mode, that is, it produces an alternating flow pattern that alternately exposes the sensor head to a dose of reference gas and then to a dose of analyte gas during each sampling cycle.

The flow pattern during the exhaling phase is sufficiently powerful to insure a fresh sample at each intake phase of the sniffing cycle. The principle, used by all breathing animals, has not been previously suggested or used for active gas sampling.

The sampling system also functions in a purge mode to restore the baseline output of the sensor. The present invention permits the use of signal processing techniques that suppress background and sensor baseline drift, and thus significantly improve the sensitivity and usefulness of chemical sensors.

The diaphragm pump used in the present invention operates in two different modes to accomplish the goals of the invention. In a DC mode, the pump produces a gas flow in one direction through a filter or other cleaning device. This cleaned air is further used as a reference gas for the second mode, known as the AC operation regime.

The second or AC operation mode performs the sniffing function by causing the direction of flow to alternate during each cycle. Gas flow in this regime is analogous to the electric current in an AC electrical circuit.

In the present invention, operation sequence first includes filling the whole sampling system with cleaned reference gas using the above referenced pumping cycle.

An intake phase of the sniffing mode follows, where a fresh sample of analyte gas from the environment of interest is brought into the sensing head. Outside air is kept from getting into the pumping chamber, avoiding contamination of the pump.

An exhaling cycle follows. The diaphragm action pushes the sample out of the sensing chamber and fills the sensing chamber again with the reference air from the buffer and the pump chambers.

The cycle starts over again by inhaling another sample.

In its simplest embodiment, the mesosniffer system consists only of a diaphragm pump working in the AC mode and a chemical sensor. The AC mode pump moves air back and forth across a sensor surface which is responsive to the desired analyte. The interaction between the analyte and the sensor is assumed to have an irreversible component, so that all the absorbed analyte is not desorbed. This causes a slowly increasing output which cannot be distinguished from baseline drift. AC signal processing eliminates the effect of the slowly changing baseline and provides an output proportional to the concentration of analyte.

BRIEF DESCRIPTION OF THE DRAWINGS

For a more complete understanding of the invention, reference is hereby made to the drawings, in which:

FIG. 1a is a schematic illustration of a sensor/sampler system of the present invention which uses two separate pumps, while

FIG. 2 is a graphical illustration of the output of the system shown in FIG. 1;

FIGS. 3a and 3b are side elevational, schematic illustration of a single chamber diaphragm pump operating in the AC regime in both intake and output modes;

FIG. 4 illustrates a multiple chamber mesopump structure;

FIG. 5 illustrates the operation of a multiple chamber diaphragm mesopump operating in the DC regime;

FIG. 6 illustrates the signal used to drive the mesopump of FIG. 5 operating in the DC regime; and FIG. 7 illustrates the operation of the mesopump of FIG. 4 in the AC regime.

DETAILED DESCRIPTION OF THE PREFERRED EMBODIMENT

Figure 1A:
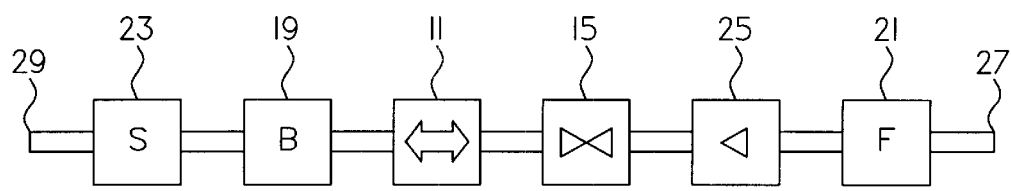
Figure 1B:
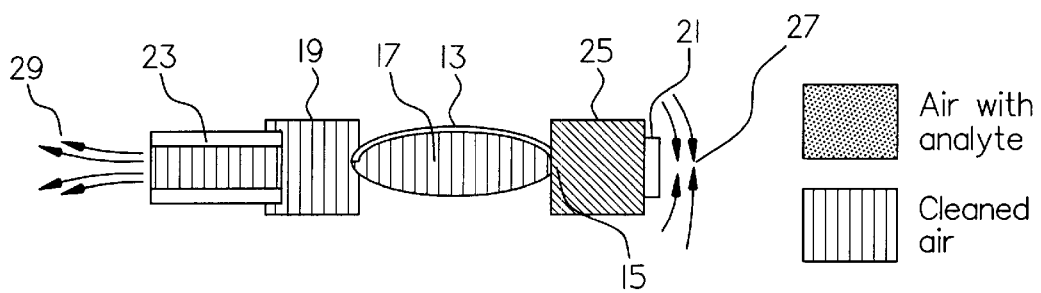
FIGS. 1b and 1c show the DC or purge pump operation.
Figure 1C:
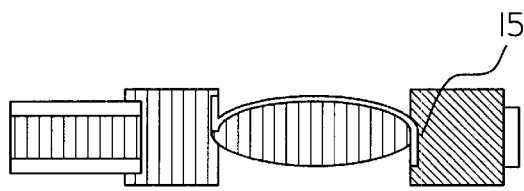
Figure 1D:
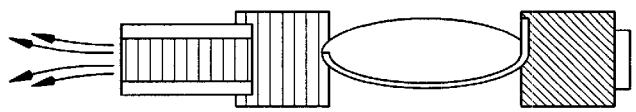
FIGS. 1d through 1g show the sequential operation of the diaphragm pump used for AC operation.
Figure 1E:
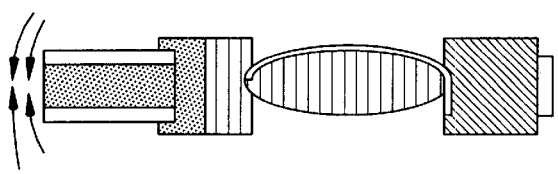
Figure 1F:
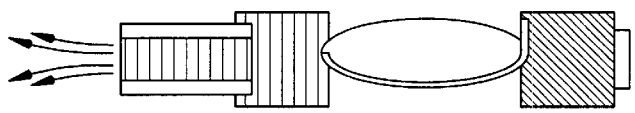
Figure 1G:
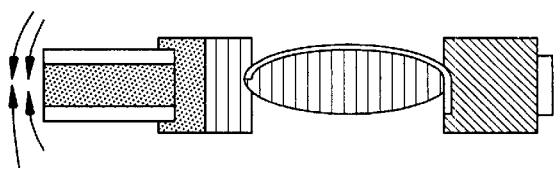

Turning now to the drawings, FIG. 1a illustrates a sampling system generally, showing a pump 11 for AC pumping, a separate pump 25 for DC pumping and a valve 15 to enable the switching from DC pumping to AC pumping. Pumps 11 and 25 and valve 15 all may be elements of the pump generically known as a mesopump, such as that described in commonly owned U.S. Pat. No. 5,835,750. Also shown are a sensing device 23 connected to pump 11 through a buffer chamber 19 and a filter 21 that cleans the gas entering the sampling system during the purging phase of the operation cycle as disclosed below. FIGS. 1b to 1f are schematic representations of the different phases of the operation cycle of the sampling system. FIG. 1b shows the purging phase of the operation. In this phase, valve 15 is opened, allowing the gas to move from the purging port 27 to the sampling port 29. The gas filling the system from purging port 27 is cleaned by filter 21, serving as a reference gas for the following phases of the operation cycle. FIG. 1c shows the end of the purging phase. Valve 21 is closed, blocking the flow to and from the purging port 27. During purging, pump 11 can contribute to the pumping action by suitable synchronization with pump 25 or can be kept inactive, in a neutral position.

FIGS. 1b, 1d, 1e, 1f and 1g show the operation of the diaphragm pump with arrows indicating the induced air flow outside the system. A volume of gas equal to the pump chamber 17 and proportionally larger than the volume of sensing chamber 23 is expelled out of the system in pump 11b Also, if the detected level of baseline drift is above a predetermined margin, heaters may be used for the purging phase to assist in desorption. A heater may be placed in buffer chamber 19, for example, to accomplish this step.

FIG. 2 illustrates the output of the system of FIG. 1. Specifically, V represents the voltage applied to the bottom electrode. More generally, it represents the position of the diaphragm, or an output derived from a flow sensor, or a diaphragm position sensor. Output (1) is the detector output for a reversible analyte-sensor interaction and Output (2) represent the detector output for an irreversible analyte-sensor interaction. With AC pumping, the sensor output provides information on the reversibility of the chemical interaction between the analyte molecules and the material of the chemical sensor. For a reversible reaction, the analyte molecules adsorbed during inhaling will be desorbed during the exhaling phase and the sensor output will be in phase with the pumping motion, shown as Output (1). At the other extreme, Output (2) illustrates the case where the analyte molecules have reacted irreversibly with the sensor material, so a dosimeter-type response is obtained. The chemical sensor output will increase during inhaling and will remain constant during exhaling, with the base-line monotonically increasing. The output of the chemical sensor will have a Fourier component at the sniffing frequency, proportional to the concentration of analyte but out of phase with the pumping action. Phase-sensitive detection or other means of correlating the pumping action with the sensor output allows the separation of the montonically increasing signal from the output, producing an output proportional to the analyte concentration. Without the active sniffing action, it would be very hard to distinguish between the analyte response and the base-line drift of the sensor. Output variations due to temperature changes, for example, will be much slower than the pumping action and can be subtracted by AC signal processing.

For irreversible interaction between the analyte and the sensor a simple AC system will provide the same benefits without the buffer chamber or the purging pump as shown in FIGS. 3a and 3b. FIGS. 3a and 3b illustrate the intake mode and output mode of a single chamber diaphragm pump operating in the AC regime. Molded pump body 31 includes a port 32 for input in FIG. 3a and output in FIG. 3b, leading to a chamber 33 which is filled or emptied by movement of diaphragm 34 upon action of a driving signal from signal source 36 to create electrostatic forces on electrodes 37. Back pressure vent 38 is included in pump body 31 to facilitate movement of diaphragm 34 and elimination of back pressure. Pump body 31 is, of course, connected via port 32 to a sensing chamber 37. The dimensions and frequency of operation are chosen so that most of the analyte is absorbed during the inhaling cycle. The resulting clean air provides the reference for the exhale cycle.

The multi-chamber mesopump described in our earlier patent is a versatile pumping system that performs both the AC and DC pumping action. FIG. 4 illustrates one mesopump channel 41, draws air into inlet 42 through filter 43, through chambers 44a, 44b, 44c and 44d to air should be stable or decrease as analyte is desorbed. If, however, an increase in the level of the analyte during exposure to clean air samples would be detected, this would indicate a drift in the base-line and could be accounted for in the measurement process.

Since these two conditions set out above are synchronized to the pumping action, it is possible to use the powerful AC signal processing technique of synchronous demodulation or phase-sensitive detection to significantly enhance the performance of the chemical sensor. In the AC gas sampling, a reference gas and a sample gas are presented to the sensor alternatively, allowing compensation for base-line drift. By integrating the output of the synchronous detector over long integration times, very low levels of signals can be detected. This technique is used to detect a modulated light sources in the presence of a large unmodulated background. Electrical chopping and synchronous detection are used to accurately measure small DC voltages that are smaller than the drifting offset voltages of the input amplifier.

The advantages of AC signal processing are well known in the art of infrared detection, and in fact are an essential element of it. In IR detection a chopper is used, and the IR sensor is alternately exposed to the shutter and to the IR source. It is commonly used to detect infrared radiation through the use of a mechanical chopper. In this example, the infrared imager alternately sees the scene and the chopper blade that presents it with a reference temperature. By phase-sensitive detection methods, the temperature of the chopper blade is subtracted from the temperature of the scene, providing a thermal image in which full contrast corresponds to a few degrees of temperature difference in the scene. The meso-sniffer of this invention has been discovered to function as the equivalent of a chopper blade to enable phase sensitive detection for a chemical sensor.

It is well known that phase-sensitive detection provides two output signals instead of one: the in-phase and the out-of-phase components of the signal. With the meso-sniffer, these two components provide information on the reversibilty of the chemical interaction between the analyte molecules and the material of the chemical sensor. We first consider the case of a chemically reversible reaction. The analyte molecules adsorbed during inhaling will be desorbed during the exhaling phase and the sensor output will be in phase with the pumping motion. See FIG. 2, detector output (1).

At the other extreme, if the analyte molecules react irreversibly with the sensor material a dosimeter-type response is obtained, as in FIG. 2, detector output (2). The chemical sensor output will increase during inhaling and will remain constant during exhaling, with the baseline monotonically increasing. The output of the chemical sensor will have a Fourier component at the sniffing frequency, proportional to the concentration of analyte but out of phase with the pumping action. Phase-sensitive detection subtracts the monotonically increasing signal from the output, producing an output proportional to the analyte concentration as shown in FIG. 2, detector output (3). Without the active sniffing action, it is very hard to distinguish the monotinic increase from baseline drift of the sensor. Output variations due to temperature changes, for example, will be much slower than the sniffing action and are much reduced by AC signal processing.

The use of phase-sensitive detection or equivalent signal processing methods significantly advances the state of the art of chemical sensing, since the present invention can be applied to many types of chemical sensors. This mode of operation is especially beneficial to the problem of land mine detection, where rapid detection of very low levels of explosives is needed.

While particular embodiments of the present invention have been illustrated and described, it is not intended to limit the invention, except as defined by the following claims.

What is claimed is:

1. A gas sampling system for detecting the presence of an analyte in the proximate atmosphere, comprising:
   a diaphragm pump having a pump chamber for moving gas into and out of said pump chamber through first and second ports, said pump including a valve at said first port having open and closed positions, said pump adapted to expel said gas at a rate greater than the rate of intake into said pump chamber;
   a buffer chamber at said second port for holding a quantity of air from said pump chamber;
   a chemical sensor head operationally connected to said buffer chamber and adapted to identify the presence of a desired analyte and produce a signal in response to the quantity identified, said chemical sensor head having a volume less than said pump chamber; and
   a sensor intake port for intaking and exhausting a sample potentially containing said analyte for contact with said sensor head upon operation of said diaphragm pump with said valve in its closed position to pump air in and out of said buffer chamber.

2. The system of claim 1, wherein said diaphragm pump is a single chamber pump.

3. The system of claim 1, wherein said diaphragm pump comprises a multiple chamber diaphragm mesopump.

4. A gas sampling system for detecting the presence of an analyte in the proximate atmosphere, comprising:
   a diaphragm pump having a pump chamber for moving gas into and out of said pump chamber through first and second ports, said pump including a valve at said first port having open and closed positions, said pump adapted to expel said gas at a rate greater than the rate of intake into said pump chamber;
   a buffer chamber at said second port for holding a quantity of air from said pump chamber;
   a chemical sensor head operationally connected to said buffer chamber and adapted to identify the presence of a desired analyte and produce a signal in response to the quantity identified, said chemical sensor head having a volume less than said pump chamber;
   a sensor intake port for intaking and exhausting a sample potentially containing said analyte for contact with said sensor head upon operation of said diaphragm pump with said valve in its closed position to pump air in and out of said buffer chamber; and
   a purging pump connected to said diaphragm pump for producing a continued flow for purging and filling said system with clean air.

5. The system of claim 4, which further includes a filter at said first port for filtering air drawn into said pump chamber when said valve is in its open position for passage of filtered air through said pump chamber, buffer chamber and sensor head to exit through said sensor intake port.

6. The system of claim 4, wherein said sample is exhausted from said sensor intake port by jet-action caused by rapid movement of said diaphragm pump.

7. The system of claim 4, wherein said diaphragm pump has a volume of gas per stroke capacity slightly larger than the volume of said sensor head.

8. The system of claim 4, wherein said pump chamber has a greater volume than said buffer chamber.

9. The system of claim 4, wherein said pump chamber has a greater volume than said buffer chamber and said buffer chamber has about the same volume as said sensor head.

10. The system of claim 4, wherein said diaphragm pump is a single chamber pump.

11. The system of claim 4, wherein said diaphragm pump comprises a multiple chamber diaphragm mesopump.

12. A gas sampling system for detecting the presence of an analyte in the proximate atmosphere, comprising:
   diaphragm pump means for pumping fluids and having pump chamber means for moving gas into and out of said pump chamber means through first and second port means for intake and exhaust of fluid from said pump chamber means, said diaphragm pump means including valve means at said first port having open and closed positions for open and closed communication with the ambient air, said pump adapted to expel said gas at a rate greater than the rate of intake into said pump chamber;
   buffer chamber means at said second port means for holding a quantity of air from said pump chamber means;
   chemical sensor head means operationally connected to said buffer chamber for identifying the presence of a desired analyte and producing a signal in response to the quantity identified, said chemical sensor head means having a volume less than said pump chamber means;
   sensor intake port means for intaking and exhausting a sample potentially containing said analyte for contact with said sensor head means upon operation of said diaphragm pump means with said valve means in its closed position to pump air in and out of said buffer chamber means; and
   filter means at said first port for filtering air drawn into said pump chamber means when said valve means is in its open position for passage of filtered air through said pump chamber means, buffer chamber means and sensor head means to exit through said sensor intake port means.

13. The system of claim 12, wherein said sample is exhausted from said sensor intake port means by jet-action caused by rapid movement of said diaphragm pump means.

14. The system of claim 12, wherein said diaphragm pump means has a volume of gas per stroke capacity slightly larger than the volume of said sensor head means.

15. The system of claim 12, wherein said pump chamber means has a greater volume than said buffer chamber means.

16. The system of claim 12, wherein said pump chamber means has a greater volume than said buffer chamber means and said buffer chamber means has about the same volume as said sensor head means.

17. The system of claim 12, wherein said diaphragm pump means is a single chamber pump means.

18. The system of claim 12, wherein said diaphragm pump means comprises a multiple chamber diaphragm mesopump means.

19. The system of claim 1, wherein a sample is exhausted from a sensor intake port by jet-action caused by rapid movement of said diaphragm pump.

\* \* \* \* \*